(12) United States Patent
Nair et al.

(10) Patent No.: US 11,224,653 B2
(45) Date of Patent: Jan. 18, 2022

(54) TREATMENT STRATEGY FOR NON-RESPONDERS TO 100MG SUBCUTANEOUS MEPOLIZUMAB

(71) Applicant: Cephalon, Inc., North Wales, PA (US)

(72) Inventors: Parameswaran Nair, Dundas (CA); Manali Mukherjee, Hamilton (CA)

(73) Assignee: Cephalon, Inc., North Wales, PA (US)

( * ) Notice: Subject to any disclaimer, the term of this patent is extended or adjusted under 35 U.S.C. 154(b) by 87 days.

(21) Appl. No.: 16/112,016

(22) Filed: Aug. 24, 2018

(65) Prior Publication Data

US 2019/0062421 A1 Feb. 28, 2019

Related U.S. Application Data

(60) Provisional application No. 62/549,564, filed on Aug. 24, 2017.

(51) Int. Cl.
| | |
|---|---|
| *A61K 39/395* | (2006.01) |
| *A61K 9/00* | (2006.01) |
| *A61P 11/06* | (2006.01) |
| *C07K 16/24* | (2006.01) |
| *C07K 14/54* | (2006.01) |
| *A61K 39/00* | (2006.01) |

(52) U.S. Cl.
CPC ........ *A61K 39/3955* (2013.01); *A61K 9/0019* (2013.01); *A61P 11/06* (2018.01); *A61K 2039/505* (2013.01); *A61K 2039/545* (2013.01); *C07K 14/5409* (2013.01); *C07K 16/244* (2013.01); *C07K 2317/24* (2013.01); *C07K 2317/76* (2013.01)

(58) Field of Classification Search
CPC .............. A61K 39/3955; A61K 9/0019; C07K 16/244; A61P 11/06
See application file for complete search history.

(56) References Cited

U.S. PATENT DOCUMENTS

| 6,056,957 A | 5/2000 | Chou et al. |
| 6,451,982 B1 | 9/2002 | Chou et al. |
| RE39,548 E | 4/2007 | Bodmer et al. |

OTHER PUBLICATIONS

Study NCT02559791, Submitted Date: Feb. 9, 2016 (v2), no author listed; available at https://clinicaltrials.gov/ct2/history/NCT02559791?V_2; 9 pages as printed.*
Medical Mutual, Nucala (mepolizumab) injection for subcutaneous use, Prior Approval Criteria, Dec. 2015; no author indicated; 6 pages; available at: https://provider.medmutual.com/PDF/RxMgmt/DrugClass/PCAT-3548%20Nucala%20PA%20Policy.pdf?*
McKinnon et al, 1997. J. Exp. Med. 186(1): 121-129.*
Benjamini et al, 1991. Immunology: A Short Course, 2nd edition, p. 40 only.*
Ferrara et al (2015. mAbs. 7(1): 32-41).*
Walsh, G., "Reslizumab, a humanized anti-IL-5 mAh for the treatment of eosinophil-mediated inflammatory conditions", Current Opinion in Molecular Therapeutics, 2009, 11(3), 329-36.
Smith SG, et al., "Increased numbers of activated group 2 innate lymphoid cells in the airways of patients with severe asthma and persistent airway eosinophilia", J Allergy Clin Immunol., 2016; 137: 75-86 e78.
Sehmi R, et al., "Role of local eosinophilopoietic processes in the development of airway eosinophilia in prednisone-dependent severe asthma", Clin Exp Allergy 2016; 46: 793-802.
Sato TA, et al., "Recombinant soluble murine IL-4 receptor can inhibit or enhance IgE responses in vivo", The Journal of Immunology, 1993; 150: 2717-2723.
Pizzichini, et al., European Respiratory Journal; Measurement of inflammatory indices in induced sputum: effects of selection of sputum to minimize salivary contamination; 1996; 9: 1174-1180.
Pizzichini, E. et al., "Indices of airway inflammation in induced sputum: reproducibility and validity of cell and fluid-phase measurements", American Journal of Respiratory and Critical Care Medicine, 1996, 154(2 Pt 1), 308-317.
Pavord I. D., et al., "Mepolizumab for severe eosinophilic asthma (DREAM): a multicentre, double-blind, placebo-controlled trial", Lancet, 2012, 380(9842), 651-659.
Ortega HG, et al.,"The MI. Mepolizumab Treatment in Patients with Severe Eosinophilic Asthma", N Engl J Med, 2014; 371: 1198-1207.
Ochkur, S.I., et al., "A sensitive high throughput ELISA for human eosinophil peroxidase: A specific assay to quantify eosinophil degranulation from patient-derived sources", Journal of Immunological Methods, 2012, 384, 10-20.
Nair, P., et al., "Eosinophil Peroxidase in Sputum Represents a Unique Biomarker of Airway Eosinophilia", Allergy, 2013, 68, 1177-1184.
Nair P.; Anti-interleukin-5 monoclonal antibody to treat severe eosinophilic asthma; N Engl J Med., Sep. 2014; 371: 1249-1251.
Mukherjee, et al.; Allergy, Asthma, and Clinical Immunology: Official Journal of the Canadian Society of Allergy and Clinical Immunology; Airway autoimmune responses in severe eosinophilic asthma following low-dose Mepolizumab therapy; 2017; 13: 2; 6 pages.
Miller et al.; American Thoracic Society /European Respiratory Society (ATS/ERS) Task Force: Standardization of Lung Function Testing; Eur Respir J 2005; 26: 319-338.
Martin CE, et al., "IL-7 /anti-IL-7 mAb complexes augment cytokine potency in mice through association with IgG-Fc and by competition with IL-7R", Blood, May 2013, 4484-4492.

(Continued)

*Primary Examiner* — Zachary C Howard
(74) *Attorney, Agent, or Firm* — BakerHostetler

(57) ABSTRACT

Disclosed herein are methods of treating severe glucocorticoid-dependent eosinophilic asthma in a subject whose asthma has been inadequately controlled with subcutaneously-administered mepolizumab. Also provided are methods of predicting responsiveness to anti-IL-5 antibody treatment in a subject having severe glucocorticoid-dependent eosinophilic asthma.

10 Claims, 6 Drawing Sheets

Specification includes a Sequence Listing.

(56) References Cited

OTHER PUBLICATIONS

Martens E, et al.,"Increased circulating interleukin-6 (IL-6) activity in endotoxin-challenged mice pretreated with anti-IL-6 antibody is due to IL-6 accumulated in antigen-antibody complexes", European J. of Immunology, 1993; 23: 2026-2029.

Liddament, M., et al., P155 higher binding affinity and invitro potency of reslizumab for interleukin-5 compared with mepolizumab. Annals of Allergy, Asthma & Immunology. 117(5): p. S68).

Juniper, et al.; Eur Respir J; Asthma quality of life during 1 year of treatment with budesonide with or without formoterol; 1999; 1038-1043.

Juniper EF, et al., "Evaluation of impairment of health related quality of life in asthma: development of a questionnaire for use in clinical trials", Thorax Feb. 1992; 47: 76-83.

Finkelman FD et al., "Anti-cytokine antibodies as carrier proteins. Prolongation of in vivo effects of exogenous cytokines by injection of cytokine-anti-cytokine antibody complexes", The Journal of Immunology 1993; 151: 1235-1244.

Chaigne B, Watier H. "Monoclonal antibodies in excess: A simple way to avoid immunogenicity in patients?", Journal of Allergy and Clinical Immunology, Sep. 2015, 814-816.

* cited by examiner

TREATMENT STRATEGY FOR NON-RESPONDERS TO 100MG SUBCUTANEOUS MEPOLIZUMAB

CROSS REFERENCE TO RELATED APPLICATIONS

This application claims priority to U.S. Provisional Application No. 62/549,564 filed on Aug. 24, 2017, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Aug. 23, 2018, is named 102085_001238_SL.txt and is 6,180 bytes in size.

TECHNICAL FIELD

The instant disclosure relates to methods of treating severe glucocorticoid-dependent eosinophilic asthma in a subject whose asthma has been inadequately controlled with subcutaneously-administered mepolizumab.

BACKGROUND

Asthma is a common, chronic inflammatory condition that affects approximately 12% of adults and 10% of children and adolescents; it is estimated that 300 million people worldwide suffer from this condition. Each day in the United States, approximately 44,000 individuals have asthma attacks, resulting in missed school/work, emergency room visits or admission to a hospital, and even death. Asthma is characterized by inflammation, and narrowing, of the air passages leading to wheezing, chest tightness, shortness of breath, and coughing. The condition described as asthma is thought to include a spectrum of disorders with a range of etiologies. Eosinophilic asthma, that is asthma in subjects who exhibit elevated levels of eosinophils in the sputum and/or blood, can be amongst the most severe and debilitating form of asthma.

Mepolizumab (Trade name: NUCALA®; an IgG1 mAb), is a commercially available anti-IL-5 mAb approved in the US as a therapy for eosinophilic asthma at a fixed dose of 100 mg administered subcutaneously every 4 weeks. Surprisingly, however, in certain subjects with severe eosinophilic asthma even though treatment with mepolizumab 100 mg SC is able to normalize levels of eosinophils in the blood it is not effective in reducing the incidence and/or severity of asthma exacerbations, requiring further medical intervention.

SUMMARY

Disclosed herein are methods of treating severe glucocorticoid-dependent eosinophilic asthma in a subject whose asthma has been inadequately controlled with subcutaneously-administered mepolizumab, the method comprising intravenously-administering a therapeutically effective dose of an anti-IL-5 antibody to the subject.

Also provided are methods of predicting responsiveness to anti-IL-5 antibody treatment in a subject having severe glucocorticoid-dependent eosinophilic asthma comprising comparing a level of IL-5 present in a pre-anti-IL-5 antibody treatment sputum sample from the subject to a level of IL-5 present in a post-anti-IL-5 antibody treatment sputum sample from the subject, wherein an increased level of IL-5 in the post-anti-IL-5 antibody treatment sputum sample from the subject compared to the pre-anti-IL-5 antibody treatment sputum sample from the subject is predictive of non-responsiveness to the anti-IL-5 antibody treatment.

Use of an anti-IL-5 antibody in the manufacture of an intravenously-administered medicament for the treatment of severe glucocorticoid-dependent eosinophilic asthma in a subject whose asthma has been inadequately controlled with subcutaneously-administered mepolizumab is also disclosed.

Also disclosed are intravenously-administered anti-IL-5 antibodies for use in the treatment of severe glucocorticoid-dependent eosinophilic asthma in a subject whose asthma has been inadequately controlled with subcutaneously-administered mepolizumab.

BRIEF DESCRIPTION OF THE DRAWINGS

The summary, as well as the following detailed description, is further understood when read in conjunction with the appended drawings. For the purpose of illustrating the disclosed methods and uses, there are shown in the drawings exemplary embodiments of the methods and uses; however, the methods and uses are not limited to the specific embodiments disclosed. In the drawings.

DETAILED DESCRIPTION OF ILLUSTRATIVE EMBODIMENTS

Figure 1:
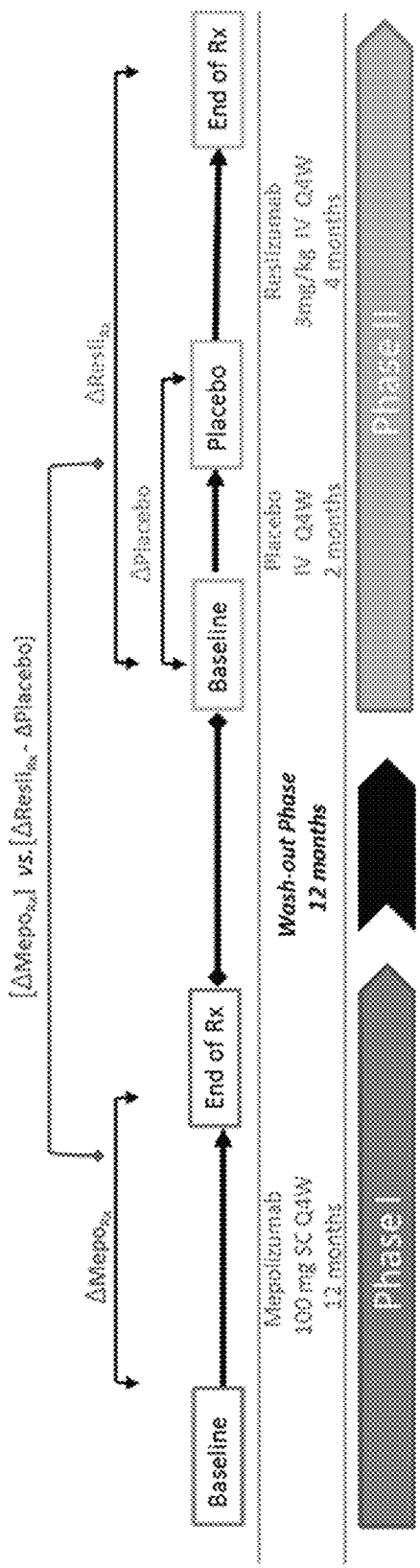
FIG. 1 illustrates a schematic of the study design described herein. The study was conducted in two distinct treatment phases. Phase I consisted of 100 mg mepolizumab treatment (the approved dose of mepolizumab (marketed as Nucala®) in the U.S. as of August 2017) (mepolizumab Rx) administered subcutaneously (SC) every four weeks (Q4W), followed by a wash-out phase, and then start of Phase II with two months of placebo (Q4W, SC) and 4 months of active drug (reslizumab, 3 mg/kg, administered intravenously (IV) by infusion Q4W) (reslizumab Rx). Clinical and exploratory outcomes were evaluated at the following 5 time points: pre-mepolizumab baseline, end of mepolizumab Rx, pre-reslizumab baseline, end of placebo, and end of reslizumab Rx.

The disclosed methods and uses may be understood more readily by reference to the following detailed description taken in connection with the accompanying figures, which form a part of this disclosure. It is to be understood that the disclosed methods and uses are not limited to the specific methods and uses described and/or shown herein, and that the terminology used herein is for the purpose of describing particular embodiments by way of example only and is not intended to be limiting of the claimed methods and uses.

Unless specifically stated otherwise, any description as to a possible mechanism or mode of action or reason for improvement is meant to be illustrative only, and the disclosed methods and uses are not to be constrained by the correctness or incorrectness of any such suggested mechanism or mode of action or reason for improvement.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the methods and uses as described herein. Where a range of numerical values is stated herein as being less than a stated value, the range is nevertheless bounded on its lower end by a non-zero value. It is not intended that the scope of the disclosed methods and uses be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed methods and uses which are, for clarity, described herein in the context of separate embodiments, may also be provided in combination in a single embodiment. Conversely, various features of the disclosed methods and uses that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "comprising" is intended to include examples encompassed by the terms "consisting essentially of" and "consisting of"; similarly, the term "consisting essentially of" is intended to include examples encompassed by the term "consisting of."

As used herein a subject with "Severe glucocorticoid-dependent eosinophilic asthma" refers to a subject exhibiting airway hyper responsiveness in addition to a level of eosinophils as $\geq 3\%$ of total sputum cells measured in a sputum sample and/or blood eosinophils $\geq 300/\mu L$ despite maintenance treatment with systemic glucocorticoids (5 to 30 mg per day of prednisone or its equivalent) as defined in the 2017 Global Initiative for Asthma (GINA) guidelines (www.ginasthma.org).

"Inadequate control" of severe glucocorticoid-dependent eosinophilic asthma in a subject refers to the continuing presence of eosinophils as >3% of the total cells in a sputum sample from the subject or ongoing asthma exacerbations following standard inhaled and/or oral glucocorticoid treatment.

As used herein, "treating" and like terms refer to a reduction in the severity and/or frequency of asthma symptoms, eliminating asthma symptoms and/or the underlying cause of said symptoms, reducing the frequency or likelihood of asthma symptoms and/or their underlying cause, and improving or remediating damage caused, directly or indirectly, by asthma. In some aspects, successful "treating" refers to a reduction in sputum eosinophilia to a value of less than 3%, a reduction of blood eosinophils to a value of less than 300/$\mu$l, or both "Therapeutically effective dose" refers to an amount of an anti-IL-5 antibody, as described herein, effective to treat severe glucocorticoid-dependent eosinophilic asthma. The therapeutically effective dose may vary according to factors such as the disease state, age, sex, and weight of the individual, and the ability of the anti-IL-5 mAb to cause a desired response in a subject.

As used herein, forced expiratory volume in 1 second ($FEV_1$) refers to the maximal amount of air that can forcefully be exhaled in one second.

As used herein, asthma control questionnaire 5 (ACQ-5) refers to a questionnaire used to measure the adequacy of asthma control and change in asthma control which occurs either spontaneously or as a result of treatment.

As used herein, forced vital capacity (FVC) refers to the volume delivered during an expiration made as forcefully and completely as possible starting from full inspiration.

Mepolizumab (SB-240563; marketed in the U.S. as NUCALA®) is a fully humanized monoclonal antibody ($IgG_1$, kappa, mAb) which is specific for human interleukin-5 (IL-5).

"Reslizumab" (SCH 55700) is a "humanized" (from rat) divalent monoclonal antibody (mAb) with an IgG4 kappa isotype, with binding affinity for a specific epitope on the human interleukin-5 (IL-5) molecule. Reslizumab is a neutralizing antibody that is believed to block IL-5 dependent cell proliferation and/or eosinophil production. Reslizumab is described in, for example, Walsh, GM (2009) "Reslizumab, a humanized anti-IL-5 mAb for the treatment of eosinophil-mediated inflammatory conditions" Current opinion in molecular therapeutics 11 (3): 329-36; U.S. Pat. No. 6,056,957 (Chou); U.S. Pat. No. 6,451,982 (Chou); U.S. Pat. No. RE39,548 (Bodmer), each of which is incorporated herein by reference. The sequences of the heavy and light chains of reslizumab are as follows:

TABLE 1

| Reslizumab sequences | |
|---|---|
| Heavy Chain (SEQ ID NO: 1) | EVQLVESGGGLVQPGGSLRLSCAVSGLSLTSNSVNWIRQAPGKGLEW VGLIWSNGDTDYNSAIKSRFTISRDTSKSTVYLQMNSLRAEDTAVYYC AREYYGYFDYWGQGTLVTVSSASTKGPSVFPLAPCSRSTSESTAALG CLVKDYFPEPVTVSWNSGALTSGVHTFPAVLQSSGLYSLSSVVTVPSS SLGTKTYTCNVDHKPSNTKVDKRVESKYGPPCPSCPAPEFLGGPSVFL FPPKPKDTLMISRTPEVTCVVVDVSQEDPEVQFNWYVDGVEVHNAKT KPREEQFNSTYRVVSVLTVLHQDWLNGKEYKCKVSNKGLPSSIEKTIS KAKGQPREPQVYTLPPSQEEMTKNQVSLTCLVKGFYPSDIAVEWESN GQPENNYKTTPPVLDSDGSFFLYSRLTVDKSRWQEGNVFSCSVMHEA LHNHYTQKSLSLSLGK |
| Light Chain (SEQ ID NO: 2) | DIQMTQSPSSLSASVGDRVTITCLASEGISSYLAWYQQKPGKAPKLLIY GANSLQTGVPSRFSGSGSATDYTLTISSLQPEDFATYYCQQSYKFPNTF GQGTKVEVKRTVAAPSVFIFPPSDEQLKSGTASVVCLLNNFYPREAKV QWKVDNALQSGNSQESVTEQDSKDSTYSLSSTLTLSKADYEKHKVY ACEVTHQGLSSPVTKSFNRGEC |

The following abbreviations are used throughout the disclosure: EoPs (eosinophil progenitor cells); IL-5 (interleukin-5); IV (intravenous); mAb (monoclonal antibodies); SC (subcutaneous); $FEV_1$ (forced expiratory volume in 1 second); ACQ (asthma control questionnaire).

Disclosed herein are methods of treating severe glucocorticoid-dependent eosinophilic asthma in a subject whose asthma has been inadequately controlled with subcutaneously-administered mepolizumab. The methods comprise intravenously-administering a therapeutically effective dose of an anti-IL-5 antibody to the subject, wherein prior to the administering, the subject's symptoms are inadequately controlled with systemic glucocorticoid and subcutaneously-administered mepolizumab. Also provided are methods of treating severe glucocorticoid-dependent eosinophilic asthma comprising, to a subject whose asthma has been inadequately controlled with subcutaneously-administered mepolizumab, intravenously-administering a therapeutically effective dose of an anti-IL-5 antibody.

Subjects having severe glucocorticoid-dependent eosinophilic asthma which is inadequately controlled with systemic glucocorticoid include those subjects exhibiting airway hyperresponsiveness and a sputum eosinophilia level of greater than or equal to 3% (i.e. greater than or equal to 3% of the total cells present in the sputum are eosinophils), a blood eosinophil level greater than or equal to 300/μl, or both. In some embodiments, prior to the intravenous administering of the anti-IL-5 antibody, the subject has a sputum eosinophilia level of greater than 3%. In some embodiments, prior to the intravenous administering of the anti-IL-5 antibody, the subject has a blood eosinophil level of greater than 300/μl. In some embodiments, prior to the intravenous administering of the anti-IL-5 antibody, the subject has a sputum eosinophilia level of greater than 3% and a blood eosinophil level of greater than 300/μl.

In some aspects of the disclosed methods, prior to the intravenous administering of anti-IL-5 antibody, the subject received subcutaneously-administered mepolizumab for at least 1 year. In some embodiments, the subcutaneously-administered mepolizumab was administered at 100 mg every four weeks.

Suitable anti-IL-5 antibodies for use in the disclosed methods include reslizumab or mepolizumab or other anti-IL-5 ligand antibodies approved for human use. In some embodiments, the methods comprise intravenously-administering a therapeutically effective dose of reslizumab to the subject, wherein prior to the administering, the subject's symptoms have been inadequately controlled with subcutaneously-administered mepolizumab. The therapeutically effective dose of reslizumab can be at least about 3.0 mg/kg administered every four weeks. In some embodiments, the methods comprise intravenously-administering a therapeutically effective dose of mepolizumab to the subject, wherein prior to the administering, the subject's symptoms have been inadequately controlled with subcutaneously-administered mepolizumab. The therapeutically effective dose of intravenously administered mepolizumab can be about 750 mg every four weeks.

The intravenously-administered anti-IL-5 antibody may lead to sputum eosinophilia of less than 3%, a blood eosinophil level of less than 300/μl, or both. In some embodiments, the intravenously-administered anti-IL-5 antibody leads to sputum eosinophilia of less than 3%. In other words, the intravenously-administered anti-IL-5 antibody can lead to an amount of eosinophils in the sputum of less than 3% of the total cells present in the sputum. In some embodiments, the intravenously-administered anti-IL-5 antibody can lead to a blood eosinophil level of less than 300/μl. In some embodiments, the intravenously-administered anti-IL-5 antibody can lead to sputum eosinophilia of less than 3% and a blood eosinophil level of less than 300/μl.

The intravenously-administered anti-IL-5 antibody can lead to a clinically significant improvement in $FEV_1$, ACQ, or both. A clinically significant improvement in $FEV_1$ may comprise a greater than or equal to about 20% increase compared to a control. A clinically significant improvement in ACQ may comprise a greater than or equal to about 50% increase compared to a control. The control may be the $FEV_1$ or ACQ value of the subject at baseline before treatment with subcutaneously administered mepolizumab or at baseline before intravenous treatment with an anti-IL-5 antibody, such as reslizumab.

Also provided is the use of an anti-IL-5 antibody in the manufacture of an intravenously-administered medicament for the treatment of severe glucocorticoid-dependent eosinophilic asthma in a subject whose asthma has been inadequately controlled with subcutaneously-administered mepolizumab.

Also provided herein is an intravenously-administered anti-IL-5 antibody for use in the treatment of severe glucocorticoid-dependent eosinophilic asthma in a subject whose asthma has been inadequately controlled with subcutaneously-administered mepolizumab.

Also provided herein are methods of predicting a subject's responsiveness to anti-IL-5 antibody treatment, wherein the subject has severe glucocorticoid-dependent eosinophilic asthma. The methods comprise comparing a level of IL-5 present in a pre-anti-IL-5 antibody treatment sputum sample from the subject with a level of IL-5 present in a post-anti-IL-5 antibody treatment sputum sample from the subject, wherein an increased level of IL-5 in the post-anti-IL-5 antibody treatment sputum sample from the subject compared to the pre-anti-IL-5 antibody treatment sputum sample from the subject is predictive of non-responsiveness to the anti-IL-5 antibody treatment. In some embodiments, the increased level IL-5 in the post-treatment sputum sample from the subject comprises greater than 100 pg/ml, greater than 110 pg/ml, greater than 120 pg/ml, greater than 130 pg/ml, greater than 140 pg/ml, or greater than 150 pg/ml.

In some embodiments, the IL-5 present in the pre-anti-IL-5 antibody sputum sample and post-anti-IL-5 antibody sputum sample comprises the total IL-5 level, which includes both "free" and immunoglobulin-bound IL-5.

In some embodiments, the methods of predicting the subject's responsiveness to anti-IL-5 antibody treatment further comprises, prior to the comparing, determining a level of IL-5 present in a pre-anti-IL-5 antibody treatment sputum sample from the subject, determining a level of IL-5 present in a post-anti-IL-5 antibody treatment sputum sample from the subject, or both.

EXAMPLES

The following examples are provided to further describe some of the embodiments disclosed herein. The examples are intended to illustrate, not to limit, the disclosed embodiments.

Methods

Trial design and patient recruitment: While mepolizumab is approved as a fixed dose of 100 mg SC, reslizumab is approved as a weight-adjusted dose of 3 mg/kg IV. Since mepolizumab was not available for clinical use by IV administration to treat asthma, the cellular and clinical outcomes of patients with severe glucocorticoid-dependent eosinophilic asthma who were treated with mepolizumab 100 mg SC and with reslizumab 3 mg/kg IV (Clinicaltrials.gov NCT02559791) were compared. The study was divided into two treatment phases separated by a wash-out period where the patients were not on any anti-IL-5 monoclonal antibody therapy (FIG. 1). The first phase (mepolizumab Rx) involved monthly treatment with 100 mg SC mepolizumab Q4W (MEA115661) (currently approved dose of mepolizumab (marketed as Nucala®) in the U.S.) for one year. 13 patients with prednisone-dependent eosinophilic asthma (sputum eosinophilia ≥3% and/or blood eosinophils ≥300/4) who had previously participated in this clinical trial of mepolizumab were invited to participate in placebo-controlled single-blind reslizumab trial. In the wash-out phase (post discontinuation of mepolizumab), all patients were reviewed monthly and were re-established on their respective optimized maintenance dose of daily oral and inhaled corticosteroids and long acting bronchodilators. After this washout period, 10 patients (5 males and 5 females, mean age 50.9±7.6 years, mean BMI 28.93±4.9) with elevated blood and sputum eosinophilia (despite mepolizumab treatment) met the inclusion criteria for the second phase (reslizumab Rx). For the second phase of the study, each patient received two monthly infusions of a placebo (which allowed the baseline disease severity of each patient, post recruitment into the trial but pre reslizumab treatment, to be established), followed by four infusions of weight-adjusted drug (reslizumab, 3 mg/kg, Q4W—currently approved dosage and administration route in the U.S.). The mean (±SD) dose of reslizumab intravenously administered at 3 mg/kg was 254.34±57.7 mg (n=10, average weight in kg: 84.8±19.2), with maximum dose of 375 mg and minimum dose of 183.6 mg. The infusions were prepared by a research pharmacist who remained blinded to the clinical details, and were administered by a study coordinator. The patients and the clinical and immunological assessors were also blinded to the sequence of allocation. All patients provided written consent.

The baseline demographic characteristics of the ten recruited patients at the start of both interventions (mepolizumab group and reslizumab group) are provided in Table 1. As shown in Table 1, the mean baseline ACQ scores, $FEV_1\%$ predicted, sputum and blood eosinophilia, and maintenance prednisone dose was comparable and well-balanced (Wilcoxon ranked test, P>0.05) prior to treatment with mepolizumab and reslizumab. All patients had: (i) evidence of asthma confirmed by bronchodilator reversibility of 12% and Δ200 ml after 200-400 μg of short-acting beta-2 agonist, and/or methacholine challenge test <8 mg/mL; and (ii) documented history of severe eosinophilia (sputum eosinophils ≥3% and/or blood eosinophils ≥300/μL) despite maintenance treatment with systemic glucocorticoids (5 to 30 mg per day of prednisone or its equivalent) before entering the study.

TABLE 2

Patient demographics

| Patient Characteristics | Mepolizumab Group (n = 10) | Reslizumab Group (n = 10) | P value |
|---|---|---|---|
| $FEV_1$ % predicted | 53.7 ± 13.7 | 47.6 ± 14.8 | 0.11 |
| VC % predicted | 66.3 ± 10.1 | 65.1 ± 15.9 | 0.57 |
| $FEV_1$/VC | 57.4 ± 9.3 | 63 ± 9.7 | 0.002 |
| ACQ-5 | 1.52 ± 0.7 | 2.04 ± 1.4 | 0.32 |
| Blood eosinophil (×10$^9$/L) | 0.349 ± 0.2 | 0.54 ± 0.2 | 0.06 |
| Sputum eosinophil (%) | 14.9 ± 18 | 30.43 ± 15 | 0.07 |
| Prednisone dose mg/daily (median, max-min) | 15 (7.5, 30) | 10 (5, 25) | 0.11 |
| Inhaled corticosteroid (mcg daily) (median, max-min) | 1750 (1000, 2500) | 1625 (1000, 2400) | 0.19 |

Data for the mepolizumab group and reslizumab group are represented as mean ± SD, unless otherwise stated; inhaled corticosteroid as equivalent of fluticasone propionate; Values are those recorded at the time patients were evaluated for mepolizumab treatment, and start of reslizumab trial.
VC (vital capacity), $FEV_1$ (forced expiratory volume in 1 second), ACQ (asthma control questionnaire).

Clinical end-points: therapeutic benefits: All end-point measurements were made at baseline (pre-mepolizumab), end of mepolizumab Rx, start of placebo (pre-reslizumab baseline), end of placebo, and end of reslizumab Rx (FIG. 1). The primary study end-points were the reduction in sputum eosinophil % and/or blood eosinophil counts (absolute). Sputum was induced and processed as described in Pizzichini E, et al. Measurement of inflammatory indices in induced sputum: effects of selection of sputum to minimize salivary contamination. *European Respiratory Journal* 1996; 9: 1174-1180. Reduction in sputum eosinophil % and/or blood eosinophil counts were analyzed per individual, and then a group analysis was performed to determine the total effect in each treatment arm. Reduction in 1) both blood and sputum eosinophils by 50% from baseline (per individual patients) or 2) blood eosinophil reduction below 300 cells/µL and sputum below 3% was considered to be a total response to anti-IL-5 therapy. One patient showed 59% reduction in absolute sputum eosinophils but his sputum eosinophil absolute values were 15% (i.e. above 3% upper normal reference). This patient was considered to be a non-responder since he remained symptomatic (explained further below). As evident from Table 1, which shows that there was no significant difference in the baseline eosinophilia at the start of both treatment regimes, non-responsiveness was not the result of a higher initial burden of eosinophilia. Secondary efficacy measures included $FEV_1$ (ATS recommendation) and asthma control questionnaire (five-question instrument, ACQ-5).

Molecular end-points: assessment of airway inflammation: Eosinophil activity in sputum was assessed by measuring eosinophil peroxidase (EPX) in the cell-free sputum supernatants using an in-house ELISA as described in Nair P., et al. Eosinophil peroxidase in sputum represents a unique biomarker of airway eosinophilia. *Allergy* 2013; 68: 1177-1184 and Ochkur S. I., et al. A sensitive high throughput ELISA for human eosinophil peroxidase: A specific assay to quantify eosinophil degranulation from patient-derived sources. *Journal of Immunological Methods* 2012; 384: 10-20. Sputum IL-5 was detected using an ELISA platform (IL-5 Duo-set, R&D Systems) modified for alkaline phosphatase-based colorimetric detection instead of horseradish peroxidase reagents to avoid interference from the endogenous peroxidases in sputum. Since the secondary detection antibodies supplied in the Duo-set were biotinylated, BluePhos® Microwell Phosphatase Substrate System (KPL Inc.) was used for color development. IL-5 levels were measured in the immunoprecipitated fraction of the sputum supernatants (as described in Mukherjee M., et al. Airway autoimmune responses in severe eosinophilic asthma following low-dose Mepolizumab therapy. *Allergy, Asthma, and Clinical Immunology: Official Journal of the Canadian Society of Allergy and Clinical Immunology* 2017; 13: 2) and in the whole supernatant. The total sputum IL-5 levels were presented as a sum of 'immunoglobulin-bound' (Ig-bound) and 'free' IL-5, respectively. As Ig-bound IL-5 can serve as a cytokine depot and increase in vivo potency, Ig-bound IL-5 was included in the total sputum IL-5 levels.

Statistical Analysis: Statistical analysis was performed using Graphpad Prism version 7.0 (La Jolla, Calif., USA) and SPSS version 23 (Chicago, Ill.). For individual drug effect, the change in the respective outcomes between placebo and drug was assessed by Wilcoxon paired analysis. For assessing significant difference in the measured outcomes between the two treatments, analysis of covariance (ANCOVA) was conducted, adjusting for baseline prednisone use.

Sputum induction and processing: Sputum was induced and processed using the method described by Pizzichini et al. 1996. Briefly, following inhalation of hypotonic aerosolized saline, cell plugs were collected from the expectorated sputum sample and processed using 0.1% dithiothreitol (SPUTOLYSIN®, Calbiochem®) and Dulbecco's Phosphate-Buffered Saline (GIBCO®). The dispersed sputum was filtered through Accufilter® filter units (Cellometrics Inc., Hamilton, ON, Canada). Following centrifugation (1500 rpm, 10 mins), cytospins were prepared from the pelleted cells on glass slides and stained with Diff-Quik® (American Scientific Products, McGaw Park, Ill., USA) for differential counts, which were enumerated by an observer blinded to the treatment period. For each cell population, means of duplicate slides were obtained (400 cells counted per slide) and expressed as a percentage of the total cell count.

Asthma Control Questionnaire 5 score: The ACQ-5 is a five-item self-completed questionnaire that has been developed as a measure of patients' asthma control and can be quickly and easily completed in clinical practice (Juniper E F, et al., *Eur Respir J* 1999; 14). The questions enquire about the frequency and/or severity of symptoms (including nocturnal awakenings recorded upon waking in the morning, activity limitation, shortness of breath, and wheeze) over the previous week. The response options for all questions consisted of a zero (no impairment/limitation) to five (total impairment/limitation) scale. The questionnaire is scored from zero to five, with greater numbers indicating poorer control and a minimally important difference of 0.5.

Spirometry: Spirometry was conducted as per the American Thoracic Society/European Respiratory Society (ATS/ERS) Task Force: Standardization of Lung Function Testing (Eur Respir J 2005; 26: 319-338) by a trained respiratory therapist. For reproducibility criteria, a minimum of 3 acceptable curves up to a maximum of 8 (depending on patient condition) were recorded.

Results

Figure 2A:
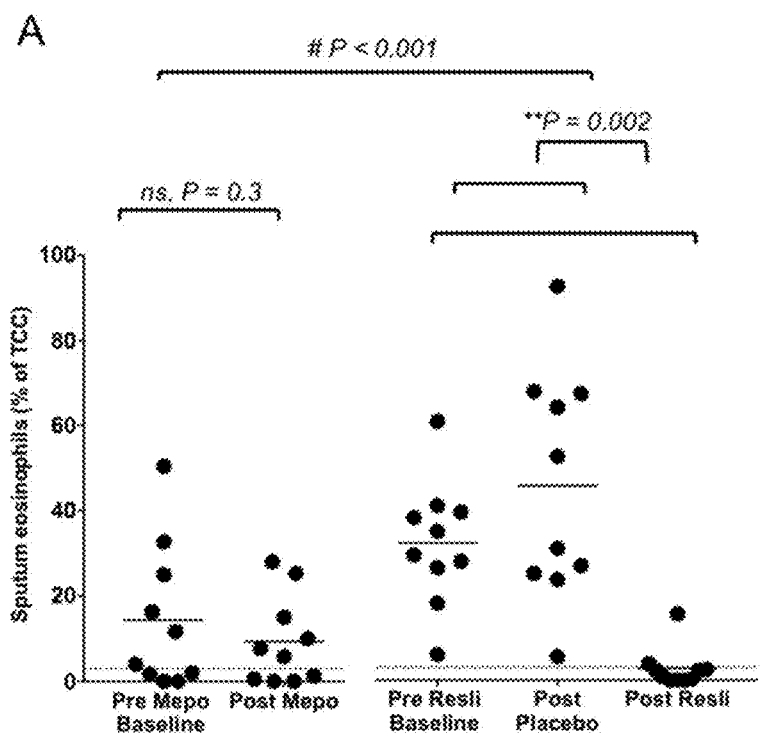
FIG. 2A and FIG. 2B illustrate the changes in eosinophilia with anti-IL-5 mAb therapy at each time point. The changes in the primary outcomes of sputum eosinophil levels (FIG. 2A) and blood eosinophil levels (FIG. 2B), and secondary outcomes for n=10 patients for all 5 time-points were measured for Phase I (mepolizumab Rx) and Phase II (reslizumab Rx) are illustrated. Treatment effect of the individual drugs was analyzed by Wilcoxon paired rank test, while difference of treatment effect between the drugs was compared by ANCOVA (adjusted for baseline prednisone dose). * indicates P values as per Wilcoxon test, ** indicates P values as per Wilcoxon test with greater significance, and # indicates P values from ANCOVA analysis.
Figure 2B:
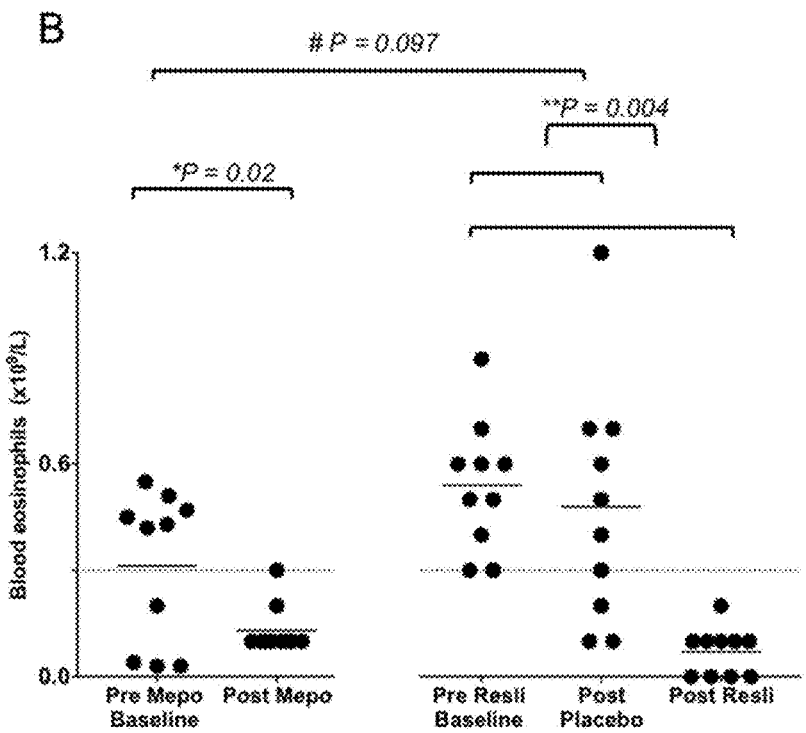

Reslizumab reduced sputum eosinophilia by 91.2% (absolute values by 29.3±14) from baseline compared to placebo (P=0.003, Wilcoxon paired test) (FIG. 2A). Treatment effect of reslizumab ($\Delta Resli_{Rx}$-$\Delta$Placebo, FIG. 1) (42.7%, absolute values) was superior to that of mepolizumab ($\Delta Mepo_{Rx}$, FIG. 1) (5.01%, absolute values) (P<0.001, ANCOVA, adjusted for baseline prednisone FIG. 2A). Of the 6 (of the 10) patients who had persistent sputum eosinophils >3% despite mepolizumab treatment, reslizumab reduced sputum eosinophil (<3% of the total cell count) in all but one (refer to FIG. 2A, dotted line represents 3% threshold). Both reslizumab and mepolizumab showed comparable efficiency in depleting blood eosinophils (P>0.05, ANCOVA) (FIG. 2B). Indeed, blood eosinophil count documented for all patients at the end of each treatment regime was <300 cells/W. Post-mepolizumab Rx: median blood eosinophil was $0.1\times10^9$/L (IQR −0.02); post reslizumab Rx: median blood eosinophil was $0.1\times10^9$/L (IQR −0.01).

Figure 3A:
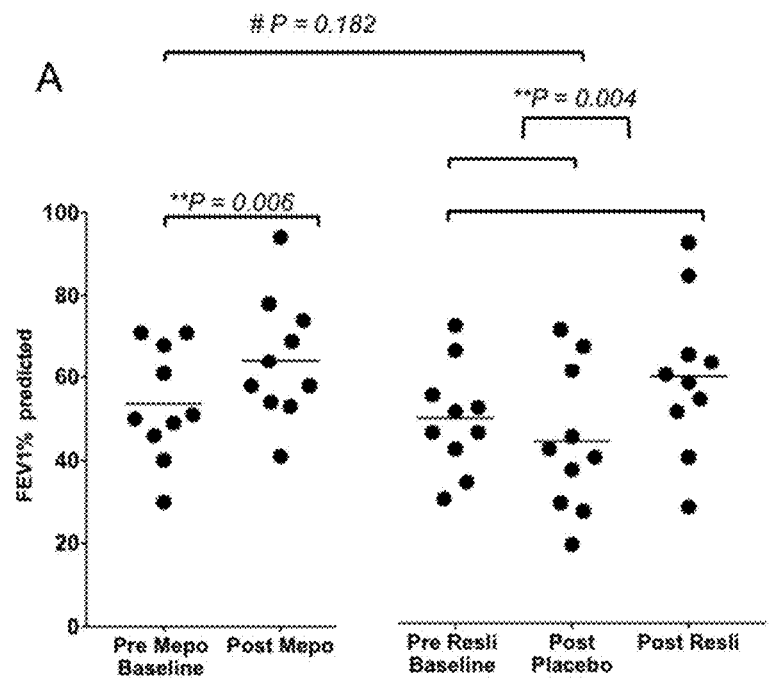
FIG. 3A and FIG. 3B illustrate changes in clinical symptoms following administration of different anti-IL-5 monoclonal antibodies as described in FIG. 1. Changes in the secondary outcomes of $FEV_1\%$ predicted (FIG. 3A) and ACQ-5 symptom score (FIG. 3B) at all 5 time-points measured for Phase I (mepolizumab Rx) and Phase II (reslizumab Rx) are illustrated. Treatment effect of the individual drugs was analyzed by Wilcoxon paired rank test, while the difference of treatment effect between the drugs was compared by ANCOVA (adjusted for baseline prednisone dose). **indicates P values as per Wilcoxon test, and # indicates P values from ANCOVA analysis.
Figure 3B:
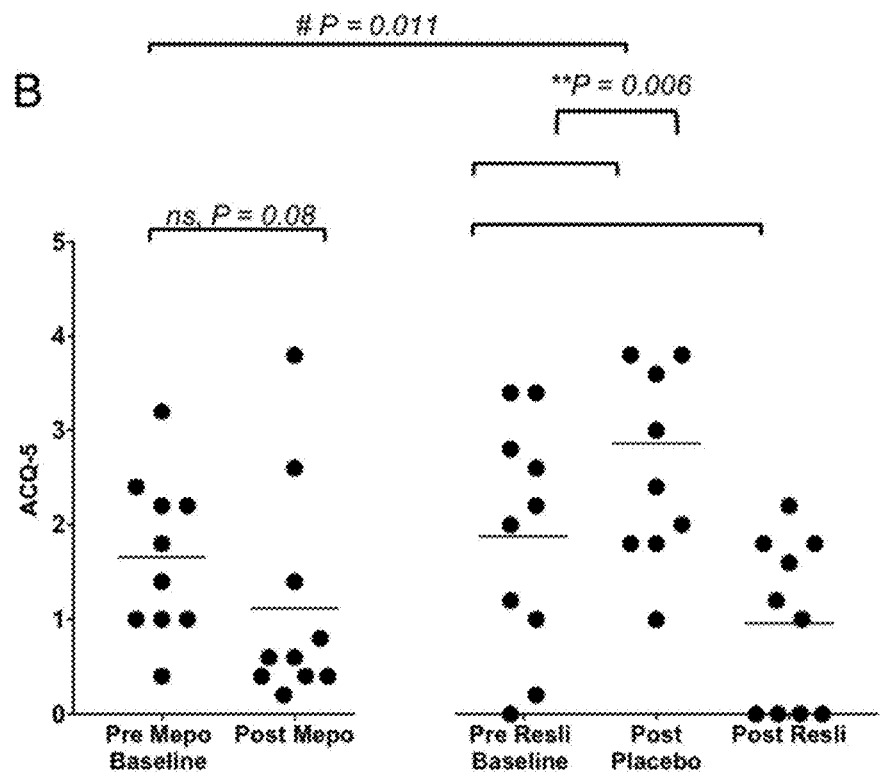

Attenuation of sputum and blood eosinophilia by reslizumab treatment was associated with significant improvement in lung function (20% increase in $FEV_1$% predicted, P=0.004, Wilcoxon paired test) and ACQ-5 symptom scores by 58.9% (P=0.006, Wilcoxon paired test) compared to its placebo control (FIG. 3A and FIG. 3B). Mepolizumab also showed significant improvement of 18.1% increase in $FEV_1$ post therapy (P=0.006, Wilcoxon paired test) but without significant improvement in ACQ scores (P=0.08) (FIG. 3A and FIG. 3B). The improvement in ACQ-5 score with reslizumab (−1.92) was significantly greater than the improvement with mepolizumab (−0.54) (FIG. 3B, ANCOVA adjusted for baseline prednisone, P=0.011). Both drugs had comparable effects on $FEV_1$ (FIG. 3A, ANCOVA, P=0.2).

Thus, 3.0 mg/kg (monthly) IV reslizumab was superior to 100 mg SC mepolizumab in reducing sputum eosinophils numbers and improving asthma control in certain severe prednisone-dependent eosinophilic asthmatic subjects.

Figure 4A:
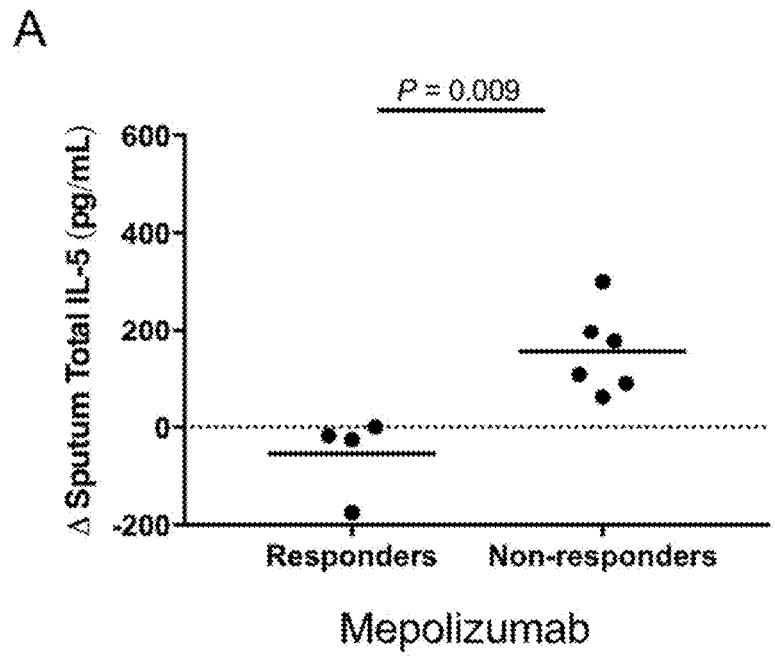
FIG. 4A and FIG. 4B illustrate the change (A) of total IL-5 (free IL-5 and immunoglobulin-bound-IL-5) levels detected in sputum of responders and non-responders of mepolizumab Rx (FIG. 4A) and reslizumab Rx (FIG. 4B). Data is plotted as the change ($\Delta$) between baseline and end-of treatment absolute values. Comparisons were made using the Mann-Whitney test.
Figure 4B:
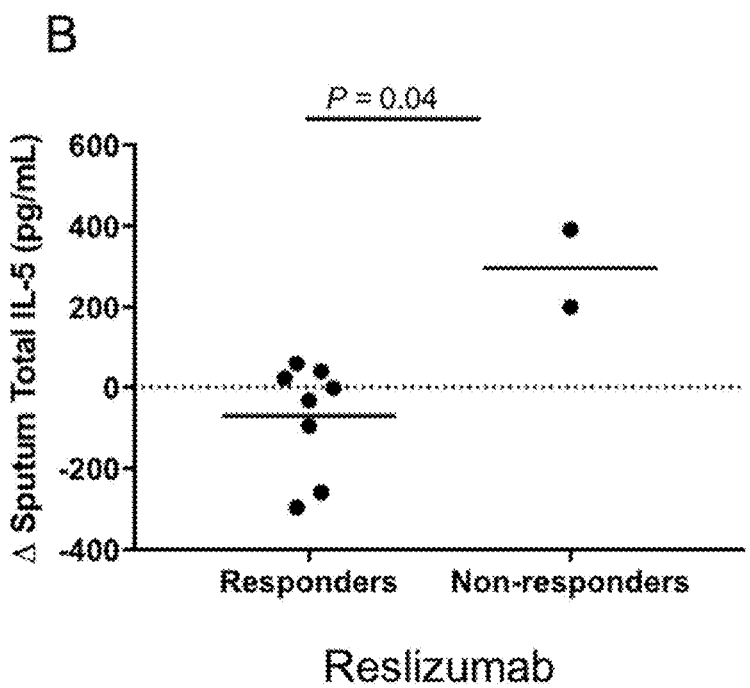

Response to anti-IL-5 therapy was considered not to be of clinical relevance if there was <50% reduction in sputum and blood eosinophils (absolute values) and/or reaching normal values (i.e. >3% sputum eosinophils, >300 cells/µL in blood), improvement in ACQ score <1.5, and/or exacerbations requiring additional prednisone dose (burst) or IV Solu-Medrol. Based on these criteria, 6 (out of 10) patients showed inadequate response to mepolizumab, and 1 for reslizumab (P=0.02, Chi-square Test). As expected, the 'non-responders' at the end of both drug treatments had sputum eosinophils >3%, except one (data not shown). It is important to note that this patient from the reslizumab study, though fulfilling the criteria of a responder (i.e., had an improvement in ACQ of 2.4 score and a 59% reduction in sputum eosinophils (blood eosinophils <300 cells/µL)) (data not shown), showed increase in sputum IL-5. This individual at the end of the reslizumab treatment had documented sputum eosinophils of 15.5% with many free granules, and has remained symptomatic. He was referred to as a non-responder and therefore, his data-point was plotted in the non-responder sub-group (FIG. 4). In the sub-group analysis, a delta increase in total IL-5 levels from baseline was demonstrable in the sputum of the non-responders at the end of both mepolizumab and reslizumab treatments (FIG. 4A and FIG. 4B). Taken together it is clear that sputum eosinophils along with change in IL-5 proteins levels were more reflective of the clinical symptoms (FIG. 4) in anti-IL-5 treated subjects compared to blood eosinophils which were seen to be depleted by the anti-IL-5 monoclonal antibodies irrespective of the associated therapeutic response (FIG. 3). Thus, an increase in interleukin-5 (IL-5) levels in the sputum post anti-IL-5 therapy was identified to be the predictor for response to anti-IL-5 therapy.

Figure 5A:
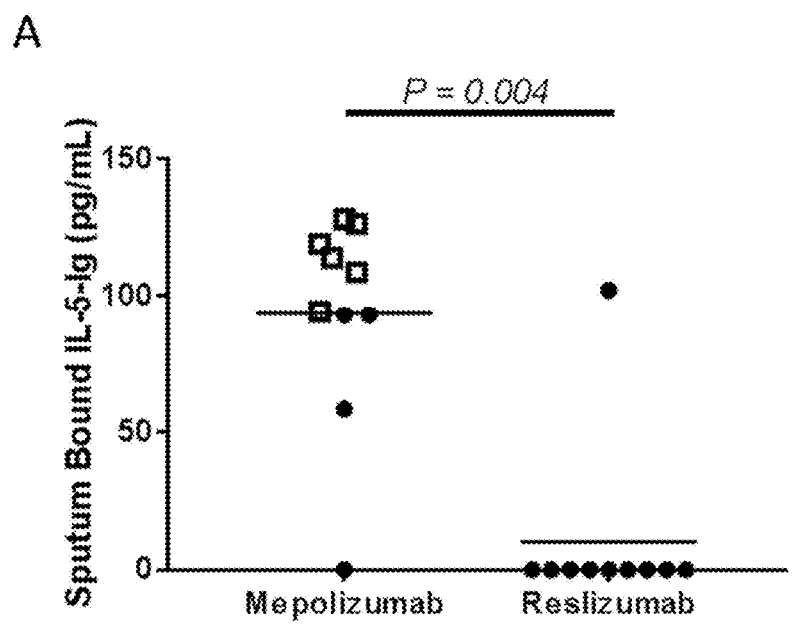
FIG. 5A, FIG. 5B, and FIG. 5C illustrate the presence of immunoglobulin-bound IL-5 complexes in the airways of non-responders to anti-IL-5 mAb therapy. Absolute values of immunoglobulin-bound IL-5 detected in immunoprecipitated immunoglobulin from sputum in all 10 patients at the end of mepolizumab Rx and the end of reslizumab Rx visit are provided in FIG. 5A. Each open square represents patients who had inadequate response to mepolizumab. Comparisons by Wilcoxon paired test. The change ($\Delta$) in immunoglobulin-bound IL-5 (FIG. 5B) and the absolute level of immunoglobulin-bound IL-5 (pg/mL) (FIG. 5C) in the sputum of non-responders vs. responders pre- and post mepolizumab Rx are provided. Comparisons were made using the Mann-Whitney test.
Figure 5B:
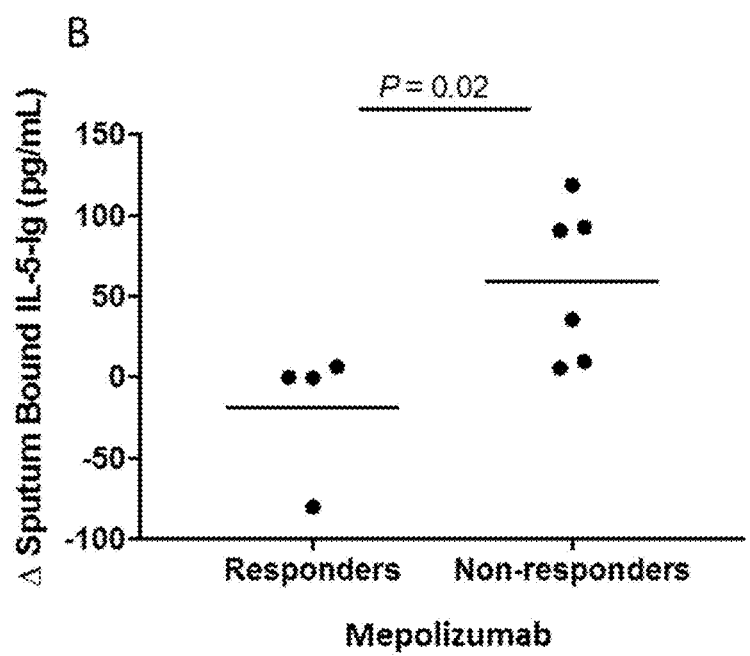
Figure 5C:
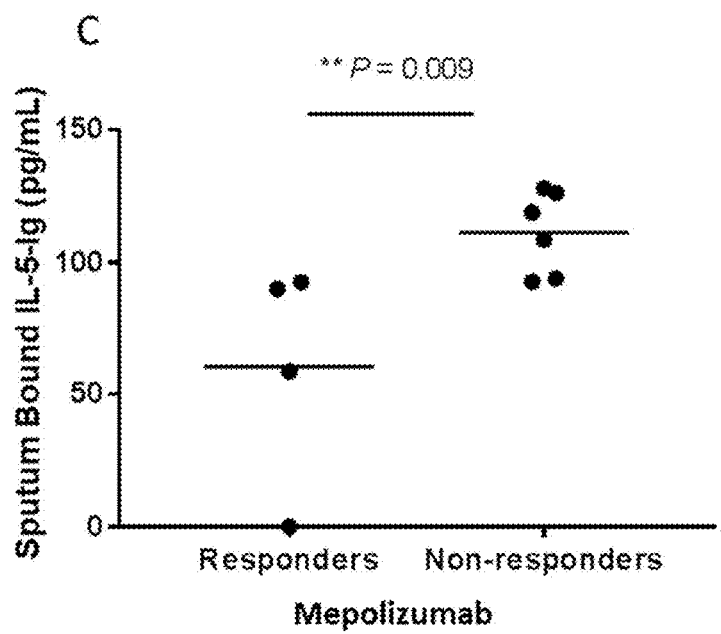

Immunoglobulin-bound IL-5 was significantly more detectable in the sputum of patients receiving mepolizumab compared to reslizumab (FIG. 5A, P=0.004, Wilcoxon), suggesting the possibility of immune-complex formation due to inadequate concentration of mepolizumab in the airways. In the non-responders for both anti-IL5 mAb therapy, Ig-bound IL-5s were detectable compared to the responders (FIG. 5B and FIG. C). Such complexes were not detectable in the sera.

Thus, the formation of IL-5-immunoglobulin complexes, detectable in the sputum, appeared to associate with non-responsiveness to mepolizumab.

SUMMARY

Reslizumab administered intravenously using a weight-adjusted dosage, was analyzed for its ability to decrease sputum eosinophilia and improve clinical outcomes. Treatment response of weight-adjusted IV reslizumab in patients previously treated with 100 mg SC mepolizumab was compared. It was found that:

1. 3.0 mg/kg (monthly) IV reslizumab was superior to 100 mg SC mepolizumab in decreasing sputum eosinophils, with improved asthma control in prednisone-dependent asthmatics. IV reslizumab also was effective at suppressing blood eosinophils.
2. The magnitude of the treatment effect of IV reslizumab was greater than that observed with one year (12 doses) of treatment with 100 mg SC mepolizumab.
3. Suppression of airway eosinophilia was associated with a clinically meaningful improvement in asthma control and $FEV_1$.
4. An increase in interleukin-5 (IL-5) levels in the sputum post anti-IL-5 therapy was a predictor for response. The levels of sputum IL-5, rather than blood eosinophil count, seem to be a determinant of response to anti-IL-5 therapy.
5. Patients with increased sputum IL-5 demonstrated IL-5 immunoglobulin complexes. A possible mechanism of non-responsiveness is the formation of IL-5-immunoglobulin complexes detectable in the sputum of mepolizumab non-responders.

As shown herein, the dose of anti-IL-5 mAb was relevant in patients with severe prednisone-dependent asthma compared to patients with mild-to-moderate asthma who require inhaled corticosteroids to control their asthma. Indeed, the dose response of mepolizumab on sputum eosinophils has been previously observed (Pavord I. D., et al. Mepolizumab for severe eosinophilic asthma (DREAM): a multicentre, double-blind, placebo-controlled trial. Lancet 2012; 380: 651-659), but this was considered to be not clinically relevant because of lack of apparent correlation with clinical outcomes of exacerbation reductions. However, the effect on the prednisone-dependent sub-population, who are likely to have higher eosinophil-mediated disease, was not examined. In fact, there is no study that reports the efficacy of reslizumab therapy in prednisone-dependent severe asthmatics, and this is the first data-set on the said patient sub-set. These patients are likely to have both local and systemically derived IL-5 from both classical (e.g. $CD4^+$ lymphocytes) and non-classical (e.g. ILC2 cells) sources. The locally derived IL-5, which may not be effectively neutralized by low dose SC anti-IL-5 mAb, could promote the local differentiation of eosinophil progenitor cells to mature eosinophils and contribute to on-going symptoms. Furthermore, in an event when the administered mAb is not in excess to the target antigen, mAb: cytokine immune complexes may be formed. These act as 'cytokine depots' and can lead to increase in in vivo potency of the bound cytokine (i.e. contribute to IL-5 related pathology), and worsen symptoms.

Early studies from the 1990s report that cytokine: anti-cytokine complexes exhibit increased in vivo half-lives, functional potency, and downstream biological activity of the bound cytokine. For instance, in a 2:1 molar ratio, IL-4:anti-IL-4 mAb increased IgE production from B cells, in comparison to recombinant IL-4 or the mAb administered alone. A more unique observation is that neutralizing mAbs are more effective than non-neutralizing mAbs in forming potent complexes. The most accepted explanation for this paradox is that neutralizing mAb in contrast to non-neutralizing mAbs bind to the active site of the cytokine and protect it from in vivo degradation/modification and increases bioavailability to its target receptors. As demonstrated herein, detectable levels of Ig-bound IL-5 were found in the sputum of mepolizumab non-responders (FIG. 5A) coupled with an associated increase in sputum IL-5 sputum eosinophil % (r=0.6, P=0.008) (data not shown). In weight-adjusted dosing with an intravenous delivery route, this phenomenon was averted. In fact, Ig-bound IL-5 was detectable in only one (out of ten) patients receiving reslizumab (FIG. 5A). A key observation was that the levels of Ig-bound IL-5 resolved in the patients post reslizumab treatment (possibly due to increased amount of mAbs reaching the target tissue). This resolution was further associated with (i) reduction in its direct downstream biological function i.e., reduction in sputum IL-5 and sputum eosinophils, and (ii) improvement in clinical response to the mAb therapy.

With this data, it is not implied that reslizumab has higher effective bioavailability than mepolizumab by virtue of the administration of a greater amount of reslizumab, but simply that more drug may have reached the airway when administered by the intravenous route. While reslizumab has been shown to have a greater affinity and in vitro potency compared to mepolizumab (Liddament, M., et al., P155 higher binding affinity and in-vitro potency of reslizumab for interleukin-5 compared with mepolizumab. *Annals of Allergy, Asthma & Immunology.* 117(5): p. S68) it cannot be determined whether this contributed to the difference in observed responses. The current discovery will aid physicians to treat patients who are poor responders/non-responders to low dose SC mepolizumab therapy with weight-adjusted IV reslizumab. It also demonstrates that monitoring sputum eosinophils is superior to blood eosinophils for assessing therapeutic response to anti-IL-5 mAbs in prednisone-dependent severe asthmatics. Finally, the discovery will allow physicians to understand the reason underlying the observed non-response (no clinical benefit) to low dose SC mepolizumab in some eosinophilic asthma patients by examining the IL-5 levels in the sputum, with a possible explanation of IL-5 immune complexes formed in vivo.

Those skilled in the art will appreciate that numerous changes and modifications can be made to the preferred embodiments of the disclosed methods and uses and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

What is claimed:

1. A method of treating severe glucocorticoid-dependent eosinophilic asthma in a subject, the method comprising:
   intravenously administering to the subject about 3 mg/kg of reslizumab, wherein
   prior to the administering, the subject's symptoms were inadequately controlled with subcutaneously-administered mepolizumab and the subject exhibited a forced expiratory volume in one second ($FEV_1$) of 32.8% to 62.4% and/or an asthma control questionnaire (ACQ) score of 0.64 to 3.44; and
   following the administering, the subject exhibits a clinically significant improvement in $FEV_1$ and ACQ, and a statistically significant reduction in sputum eosinophil levels and/or blood eosinophil counts.

2. The method of claim 1, wherein, prior to the administering, the subject had a sputum eosinophilia level of greater than 3%.

3. The method of claim 1, wherein, prior to the administering, the subject's blood eosinophil levels were greater than 300/µl.

4. The method of claim 1, wherein, prior to the administering, the subject received subcutaneously-administered mepolizumab for at least 1 year.

5. The method of claim 4, wherein the subject received 100 mg of subcutaneously-administered mepolizumab every four weeks.

6. The method of claim 1, wherein the reslizumab is administered every four weeks.

7. The method of claim 1, wherein, following the administering, the level of sputum eosinophils are less than 3%, the blood eosinophil counts are less than 300/µl, or both.

8. The method of claim 7, wherein the blood eosinophil counts are at least 50% compared to a pretreatment level.

9. The method of claim 1, wherein the clinically significant improvement in $FEV_1$ comprises a greater than or equal to 20% increase compared to a control.

10. The method of claim 1, wherein the clinically significant improvement in ACQ comprises a greater than or equal to 50% increase compared to a control.

* * * * *

SEQUENCE LISTING

```
<160> NUMBER OF SEQ ID NOS: 2

<210> SEQ ID NO 1
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Ser Leu Thr Ser Asn
            20                  25                  30

Ser Val Asn Trp Ile Arg Gln Ala Pro Gly Lys Gly Leu Glu Trp Val
        35                  40                  45

Gly Leu Ile Trp Ser Asn Gly Asp Thr Asp Tyr Asn Ser Ala Ile Lys
    50                  55                  60

Ser Arg Phe Thr Ile Ser Arg Asp Thr Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Arg Glu Tyr Tyr Gly Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Ser
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255
```

```
Cys Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Asn Ser Leu Gln Thr Gly Val Pro Ser Arg Phe Ser Gly
    50                  55                  60

Ser Gly Ser Ala Thr Asp Tyr Thr Leu Thr Ile Ser Ser Leu Gln Pro
65                  70                  75                  80

Glu Asp Phe Ala Thr Tyr Tyr Cys Gln Gln Ser Tyr Lys Phe Pro Asn
                85                  90                  95

Thr Phe Gly Gln Gly Thr Lys Val Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```